(12) United States Patent
Yamanishi et al.

(10) Patent No.: US 6,235,875 B1
(45) Date of Patent: *May 22, 2001

(54) PROCESS FOR PRODUCING DEPSIPEPTIDE DERIVATIVES AND NOVEL INTERMEDIATES THEREFOR

(75) Inventors: Ryo Yamanishi, Tsukuba; Masaru Ohgaki, Kobe, both of (JP)

(73) Assignee: Fujisawa Pharmaceutical Co., Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,743
(22) PCT Filed: Sep. 24, 1997
(86) PCT No.: PCT/JP97/03417
§ 371 Date: Apr. 6, 1999
§ 102(e) Date: Apr. 6, 1999
(87) PCT Pub. No.: WO98/15523
PCT Pub. Date: Apr. 16, 1998

(30) Foreign Application Priority Data

Oct. 7, 1996 (JP) .................................................. 8/286047

(51) Int. Cl.$^7$ ............................. A61K 38/15; C07K 11/00
(52) U.S. Cl. ............................. 530/330; 514/18; 514/16; 530/317; 530/328
(58) Field of Search ..................................... 530/317, 328, 530/330, 323; 514/16, 18

(56) References Cited

U.S. PATENT DOCUMENTS

| | | | |
|---|---|---|---|
| 5,514,773 | 5/1996 | Nishiyama et al. | 530/317 |
| 5,646,244 | 7/1997 | Nishiyama et al. | 530/317 |
| 5,717,063 | * 2/1998 | Scherkenbeck et al. | 530/323 |
| 5,777,075 | * 7/1998 | Beck et al. | 530/330 |
| 5,856,436 | 1/1999 | Nishiyama et al. | 530/317 |

* cited by examiner

Primary Examiner—Richard L. Raymond
Assistant Examiner—Sudhaker B. Patel
(74) Attorney, Agent, or Firm—Oblon, Spivak, McClelland, Maier & Neustadt, P.C.

(57) ABSTRACT

An industrially excellent alternative process for producing cyclodepsipeptide derivatives, as represented in formula (1), having an excellent vermicidal activity as an animal and human anthelmintic, wherein $R_1$ represents hydrogen or a hydroxyl-protective group; $R_2$ represents a carboxyl group optionally protected; $R_3$, $R_4$, $R_7$ and $R_8$ represent each a lower alkyl, aryl or (un)substituted aralkyl; and $R_5$, $R_6$, $R_9$ and $R_{10}$ represent each a lower alkyl.

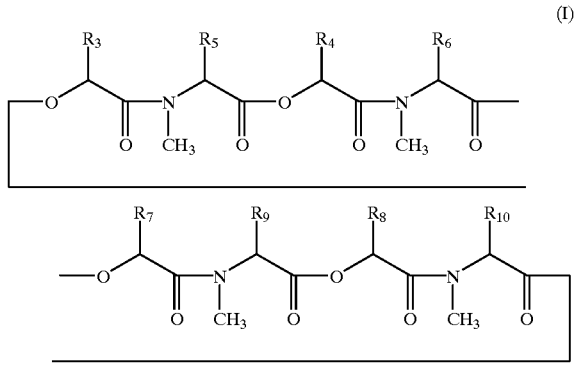

5 Claims, No Drawings

PROCESS FOR PRODUCING DEPSIPEPTIDE DERIVATIVES AND NOVEL INTERMEDIATES THEREFOR

TECHNICAL FIELD

This invention relates to an alternative process for producing a cyclodepsipeptide derivative having vermicidal activity and to novel intermediates for synthesis of said depsipeptide derivative.

BACKGROUND ART

The cyclodepsipeptide derivative of this invention, represented by the following general formula (I), is known to be a compound having high vermicidal activity and finds application as an anthelmintic in animals and man. In the conventional synthesis of such cyclodepsipeptides, the cyclization reaction involved is invariably carried out in the manner of amide bond formation to construct a cyclic structure (WO 93/19053, Kokai Tokkyo Koho H5-320148, EP-626375, EP-626376).

For example, a cyclization process using the following route is known (WO 93/19053).
Conventional Route:

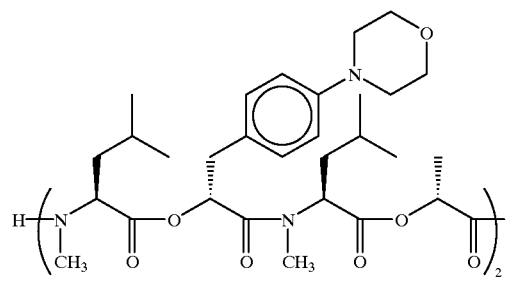

↓

-continued

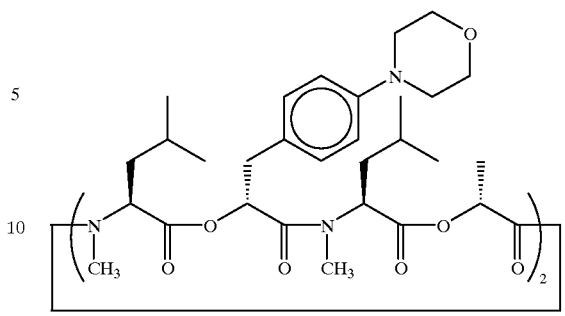

DISCLOSURE OF INVENTION

The inventors of this invention studied the possible cyclization reaction by ester bond formation in the production process for such cyclodepsipeptides and have developed this instant invention.

The depsipeptide of this invention can be represented by the following general formula (I).

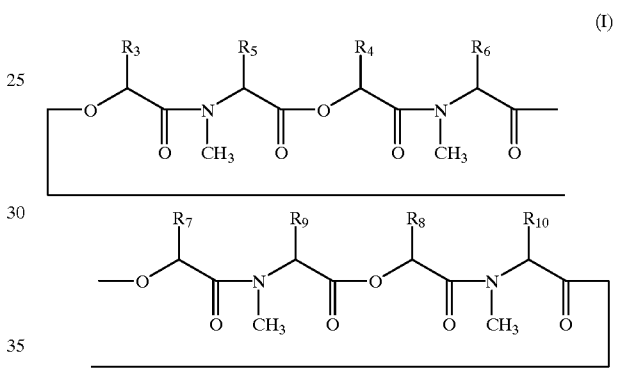

In accordance with this invention, the objective compound (I) or its salt can be produced by a process involving the following series of steps.

Process 1
Step 1

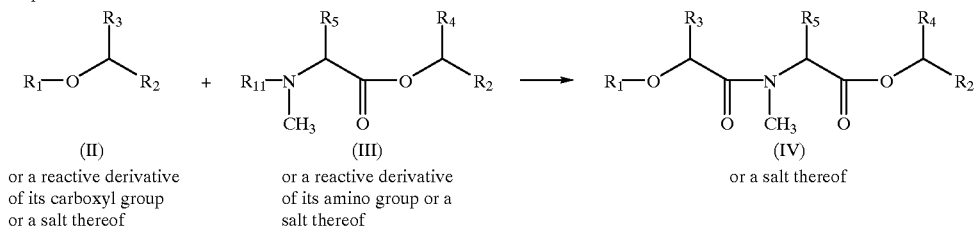

(II)
or a reactive derivative
of its carboxyl group
or a salt thereof (III)
or a reactive derivative
of its amino group or a
salt thereof (IV)
or a salt thereof Step 2

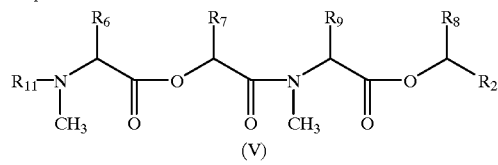
(V)
or a reactive derivative of its carboxyl group or a salt thereof

↓ ←

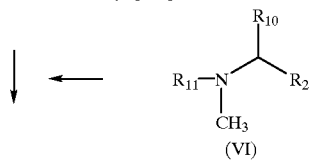
(VI)
or a reactive derivative of its
amino group or a salt thereof

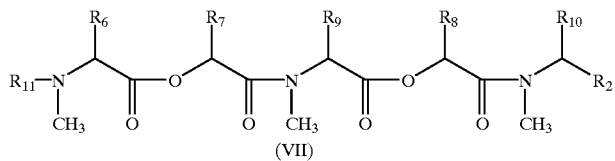
(VII)
or a salt thereof

Step 3

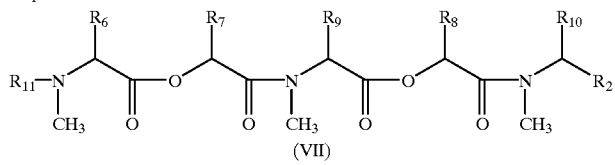
(VII)
or a reactive derivative of its amino group or a salt thereof

↓ ←

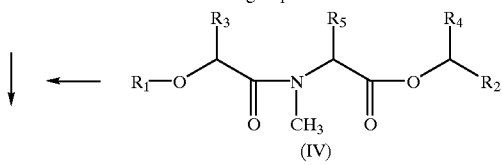
(IV)
or a reactive derivative of its
carboxyl group or a salt thereof

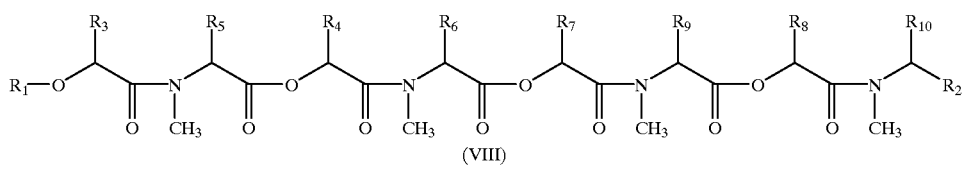
(VIII)
or a salt thereof

Step 4

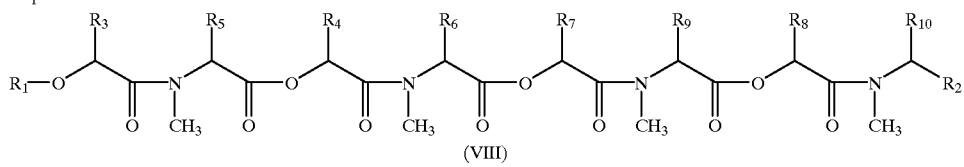
(VIII)
or a reactive derivative of its carboxyl group or a salt thereof

-continued

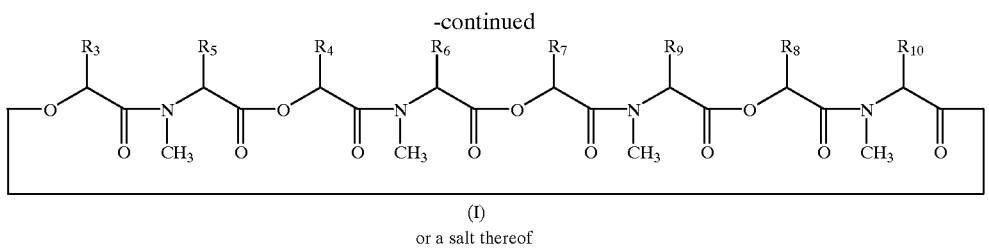

(I)

or a salt thereof

[In the respective formulas, $R_1$ represents hydrogen or a hydroxyl-protecting group; $R_2$ represents a carboxyl group or a protected carboxyl group; $R_3$, $R_4$, $R_7$ and $R_9$ each represents a lower alkyl group, an aryl group, or a substituted or unsubstituted aralkyl group; $R_5$, $R_6$, $R_9$ and $R_{10}$ each represents a lower alkyl group; $R_{11}$ represents hydrogen or an amino-protecting group]

Compound (II) in the above process includes known compounds and novel compounds, and compounds (IV), (VII) and (VIII), inclusive of their reactive derivatives, as well as salts thereof are novel compounds.

Throughout this specification, amino acids, peptides, protective groups, condensing agents, etc. are indicated by using the abbreviations recommended by IUPAC-IUB (a committee on biochemical nomenclature) which are in common use.

Moreover, the amino acids and their residues as indicated by such abbreviations mean the L-configured compounds and residues unless otherwise specified, and D-configured compounds and residues are indicated by the symbol D-.

The abbreviations used in the invention are as follows.

MeLeu: methylleucine p-MorPhLac: 2-hydroxy-3-(4-morpholinophenyl)-propionic acid [β-(p-morpholinophenyl)lactic acid]

Lac: 2-hydroxypropionic acid [lactic acid]

MOM: methoxymethyl

Boc: t-butoxycarbonyl

Bzl: benzyl

The preferred salts of Compounds (I), (II), (III), (IV), (V), (VI), (VII) and (VIII) include conventional nontoxic salts, which are salts with various bases and acid addition salts. More particularly, there can be mentioned salts with inorganic bases, such as alkali metals (e.g. sodium salt, potassium salt, cesium salt, etc.) and alkaline earth metals (e.g. calcium salt, magnesium salt, etc.), and ammonium salts; salts with organic bases, such as organic amine salts (e.g. triethylamine salt, pyridine salt, picoline salt, ethanolamine salt, triethanolamine salt, dicyclo-hexylamine salt, N,N'-dibenzylethylenediamine salt, etc.); inorganic acid addition salts (e.g. hydro-chloride, hydrobromide, sulfate, phosphate, etc.); organic carboxylic acid addition salts or organic sulfonic acid addition salts (e.g. formate, acetate, trifluoroacetate, maleate, tartrate, methanesulfonate, benzenesulfonate, p-toluenesulfonate, etc.); and salts with basic or acidic amino acids (e.g. arginine salt, aspartate, glutamate, etc.).

The preferred examples and the explanations of the various definitions made in the foregoing as well as the following disclosure and falling under the scope of the invention are now given in detail.

The preferred "hydroxyl-protecting group" includes but is not limited to acyl, substituted or unsubstituted aralkyl, which will be described in detail hereinafter, lower alkoxy (lower)alkyl, carbamoyl and silyl.

The preferred examples of the "acyl" mentioned just above are aliphatic acyl groups and acyl groups having an aromatic ring or heterocycle. The preferred examples of such acyl include but are not limited to:

lower alkanoyl groups such as formyl, acetyl, propionyl, butyryl, isobutyryl, valeryl, isovaleryl, oxalyl, succinyl, pivaloyl, etc.;

lower alkoxycarbonyl groups such as methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, hexyloxycarbonyl, etc.;

lower alkanesulfonyl groups such as mesyl, ethanesulfonyl, propanesulfonyl, isopropanesulfonyl, butanesulfonyl, etc.;

aroyl groups such as benzoyl, toluoyl, xyloyl, naphthoyl, phthaloyl, indancarbonyl, etc.;

ar(lower)alkanoyl groups such as phenylacetyl, phenylpropionyl, etc.; and ar(lower)alkoxycarbonyl groups such as benzyloxycarbonyl, phenethyloxycarbonyl, etc.

The above-mentioned acyl groups may each have one or more suitable substituent groups such as chlorine, bromine, fluorine and iodine.

The preferred examples of said lower alkoxy(lower)alkyl are 1-methyl-1-methoxyethyl, methoxy-methyl and methoxypropyl, among others.

The preferred "protected carboxyl" includes esterified carboxyl such as the following "esterified carboxyl" groups. The preferred ester moiety of such esterified carboxyl includes lower alkyl esters optionally containing one or more suitable substituent groups. For example, there can be mentioned lower alkyl esters such as methyl ester, ethyl ester, propyl ester, isopropyl ester, butyl ester, isobutyl ester, tert-butyl ester, pentyl ester, tert-pentyl ester, hexyl ester, etc.; lower alkanoyloxy(lower)alkyl esters such as acetoxymethyl ester, propionyloxymethyl ester, butyryloxymethyl ester, valeryloxymethyl ester, pivaloyloxymethyl ester, hexanoyloxymethyl ester, etc.; mono(or di- or tri-)halo(lower)alkyl esters such as 2-iodoethyl ester, 2,2,2-trichloroethyl ester, etc.; lower alkenyl esters such as vinyl ester, allyl ester, etc.; ar(lower)alkyl esters optionally having one or more substituent groups, such as benzyl ester, 4-methoxybenzyl ester, 4-nitrobenzyl ester, phenethyl ester, trityl ester, benzhydryl ester, bis(methoxy-phenyl)methyl ester, 3,4-dimethoxybenzyl ester, 4-hydroxy-3,5-di-tert-butylbenzyl ester, etc.

The protective group for said "protected carboxyl" includes those protective groups which are conventionally used for temporary protection of carboxyl groups in the field of amino acid or peptide chemistry.

The "lower" means the range of 1~6 carbon atoms, preferably 1~4 carbon atoms, unless otherwise specified.

The preferred "lower alkyll" includes straight-chain or branched-chain alkyl groups such as methyl, ethyl, n-propyl, isopropyl, butyl, isobutyl, tert-butyl, pentyl, neopentyl and hexyl.

The preferred "aryl" includes but is not limited to phenyl, naphthyl, and lower alkyl-substituted phenyl (e.g. tolyl, mesityl, cumenyl, xylyl, diethylphenyl, diisopropylphenyl, di-tert-butylphenyl, etc.).

The "substituted or unsubstituted aralkyl" means said lower alkyl group having an aryl group in an arbitrary position and includes benzyl, phenethyl, 3-phenylpropyl, benzhydryl, and trityl, to mention a few preferred examples.

The "aralkyl" for $R_3$, $R_7$ may have 1 or more substituent groups.

The preferred substituent groups for "substituted benzyl", among said "substituted or unsubstituted aralkyl", includes but is not limited to hydroxyl, lower alkoxy, lower alkoxy (lower)alkoxy, lower alkoxy-(lower)alkoxy(lower)alkoxy, heterocyclic(lower)-alkoxy, lower alkyl, amino, mono- or di-substituted lower alkylamino, cyclic amino, nitro, and halogen such as fluorine, chlorine, bromine or iodine. One or more of such substituent groups may be present.

The above preferred "lower alkoxy" includes but is not limited to methoxy, ethoxy, propoxy, isopropoxy, butoxy, isobutoxy, pentyloxy, isopentyloxy, and hexyloxy.

The above preferred "lower alkoxy(lower)alkoxy" includes but is not limited to methoxymethoxy, methoxyethoxy, methoxypropoxy, and ethoxyisopropoxy.

The above preferred "lower alkoxy(lower)-alkoxy(lower) alkoxy" includes but is not limited to methoxymethoxyethoxy, methoxyethoxyethoxy, methoxyethoxypropoxy, and ethoxymethoxyisopropoxy.

The above preferred "heterocyclic(lower)alkoxy" includes but is not limited to pyridylmethoxy and furanyl-methoxy.

The above preferred "mono- or di-substituted lower alkylamino" is a group derived from a lower alkylamino group by substitution with 1 or 2 lower alkyl groups such as methyl, ethyl, isopropyl, t-butyl, t-pentyl, etc., thus including methylamino, ethylamino, dimethylamino, diethylamino, di-n-propylamino, diisopropylamino, and dibutylamino, to mention just a few preferred examples.

The above preferred "cyclic amino" is an aromatic or alicyclic group having at least one nitrogen atom as the hetero-atom and may be either saturated or unsaturated and either monocyclic or fused polycyclic. Moreover, it may contain one or more additional hetero-atoms such as nitrogen, oxygen, sulfur, etc. within the ring. In addition, this cyclic amino group may be a spiro ring group or a bridged ring group. Although there is no particular limitation on the number of constituent atoms, this cyclic amino may for example be a 3- through 8-membered ring in the case of a monocyclic system or a 7- through 11-membered ring in the case of a bicyclic system.

As examples of the cyclic amino, there can be mentioned saturated or unsaturated monocyclic groups having one nitrogen atom as the hetero-atom, such as 1-azetidinyl, pyrrolidino, 2-pyrrolin-1-yl, 1-pyrrolyl, piperidino, 1,4-dihydropyridin-1-yl, 1,2,5,6-tetrahydropyridin-1-yl, homopiperidino, etc.; saturated or unsaturated monocyclic groups containing 2 or more nitrogen atoms as the hetero-atoms, such as 1-imidazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropyrimidin-1-yl, perhydropyrimidin-1-yl, 1,4 -diazacycloheptan-1-yl, etc.; saturated or unsaturated monocyclic groups containing 1~3 nitrogen atoms and 1~2 oxygen atoms as the hetero-atoms, such as oxazolidin-3-yl, 2,3-dihydroisoxazol-2-yl, morpholino, etc.; saturated or unsaturated monocyclic groups containing 1~3 nitrogen atoms and 1~2 sulfur atoms as the hetero-atoms, such as thiazolidin-3-yl, iso-thiazolin-2-yl, thiomorpholino, etc.; fused cyclic groups such as indol-1-yl, 1,2-dhydrobenzimidazol-1-yl, perhydrospiro[1,2-a]pyrazin-2-yl, etc.; spiro ring groups such as 2-azaspiro[4,5]decan-2-yl etc.; and bridged heterocyclic groups such as 7-azabicyclo-[2,2,1]heptan-7-yl, among others.

The above-mentioned "cyclic amino which may be substituted" includes pyrrolizino, morpholino, 1-piperazino, 4-methylpiperazino and piperidino, to mention just a few preferred specific examples.

The "amino-protecting group" includes acyl groups, for example lower alkanoyl groups such as formyl, acetyl, propionyl, pivaloyl, hexanoyl, etc., mono(or di- or tri-) halo (lower) alkanoyl groups such as chloroacetyl, bromoacetyl, dichloroacetyl, trifluoroacetyl, etc., lower alkoxycarbonyl groups such as methoxycarbonyl, ethoxycarbonyl, propoxycarbonyl, t-butoxycarbonyl, t-pentyloxycarbonyl, hexyloxycarbonyl, etc., carbamoyl, aroyl groups such as benzoyl, toluoyl, naphthoyl, etc., ar(lower)alkanoyl groups such as phenylacetyl, phenylpropionyl, etc., aryloxycarbonyl groups such as phenoxycarbonyl, naphthyloxycarbonyl, etc., aryloxy(lower)alkanoyl groups such as phenoxyacetyl, phenoxypropionyl, etc., arylglyoxyloyl groups such as phenylglyoxyloyl, naphthylglyoxyloyl, etc., and optionally substituted ar(lower)alkoxycarbonyl groups such as benzyloxycarbonyl, phenethyloxycarbonyl, p-nitrobenzyloxycarbonyl, etc., among others; substituted or unsubstituted ar(lower)alkylidene groups such as benzylidene, hydroxybenzylidene etc.; and ar(lower)alkyl groups such as mono(or di- or tri-)phenyl (lower) alkyl groups, e.g. benzyl, phenethyl, benzhydryl, trityl, etc.

Among the above-mentioned amino-protecting groups are those protective groups which are conventionally used for provisional protection of amino groups in amino acid or peptide chemistry.

The process for producing the objective compound (I) is now described in detail.

Process
Step 1

Compound (IV) or a salt thereof can be produced by reacting compound (II) or a reactive derivative of its carboxyl group, or a salt thereof, with compound (III) or a reactive derivative of its amino group or a salt thereof.

This reaction can be conducted in the conventional manner to convert the carboxyl group to the amide bond:

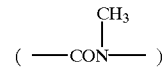

The preferred reactive derivative of the carboxyl group of compound (II) includes acid halides, acid anhydrides, activated amides, activated esters, etc. The preferred examples are the acid chloride; acid azide; mixed acid anhydrides with such acids as substituted phosphoric acids (e.g. dialkyl phosphate, phenyl phosphate, diphenyl phosphate, dibenzyl phosphates halophosphoric acids, etc.), dialkyl phosphite, sulfurous acid, thiosulfuric acid, sulfuric acid, alkyl carbonates, lower alkanesulfonic acids (e.g. methanesulfonic acid, ethanesulfonic acid, etc.), aliphatic carboxylic acids (e.g. acetic acid, propionic acid, butyric acid, isobutyric acid, pivalic acid, pentanoic acid, isopentanoic acid, 2-ethylbutyric acid, trichloroacetic acid, etc.) or aromatic carboxylic acids (e.g. benzoic acid etc.); symmetric acid anhydride; active amides with imidazole, 4-substituted imidazole, dimethylpyrazole, triazole or tetrazole; and esters such as active esters (e.g. cyanomethyl ester, methoxymethyl ester, dimethyliminomethyl[ $(CH_3)_2N^+=CH—$ ] ester, vinyl ester, propargyl ester, p-nitrophenyl ester, 2,4-dinitrophenyl ester, trichlorophenyl ester, pentachlorophenyl ester, pentafluorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester, 8-quinolylthio ester, etc.), and esters with N-hydroxyl compounds (e.g. N,N-dimethylhydroxylamine, 1-hydroxy-2-(1H)-pyridone, N-hydroxysuccinimide, N-hydroxyphthalimide, 1-hydroxy-1H-benzotriazole, etc.). Those reactive derivatives can be selectively used according to the species of compound (II).

The preferred reactive derivative of the amino group of compound (III) includes Schiff base-type imine and enamine tautomers which can be obtained by reacting compound (III) with carbonyl compounds such as aldehydes or ketones; silyl derivatives which can be obtained by reacting compound (III) with silyl compounds such as bis(trimethylsilyl)acetamide, mono(trimethylsilyl)acetamide, bis(trimethylsilyl)-urea, etc.; and the derivative which can be obtained by reacting compound (III) with phosphorus trichloride or phosgene.

This reaction is generally conducted in the common solvent such as water, alcohol (e.g. methanol, ethanol, etc.), acetone, dioxane, tetrahydrofuran, acetonitrile, chloroform, dichloromethane, ethylene chloride, ethyl acetate, N,N-dimethylformamide, pyridine, etc., or an organic solvent, other than the above, which does not interfere with the reaction. Among those solvents, hydrophilic solvents can be used in admixture with water.

There is no particular limitation on the reaction temperature but the reaction is generally carried out under cooling, at room temperature or at elevated temperature.

When compound (II) is used either in its free form or in the salt form in conducting this reaction, the reaction is preferably carried out in the presence of a conventional condensing agent. The condensing agent includes but is not limited to carbodiimides and salts thereof (e.g. N,N'-dicyclohexylcarbodiimide, N-cyclohexyl-N'-morpholinoethylcarbodiimide, N-cyclo-hexyl-N'-(4-diethylaminocyclohexyl)carbodiimide, N,N'-diethylcarbodiimide, N,N'-diisopropylcarbodi-imide, N-ethyl-N'-(3-dimethylaminopropyl)carbodiimide or its hydrochloride, diphenylphosphoryl azide, diethylphosphoryl cyanide, bis(2-oxo-3-oxazolidin-yl)phosphinic chloride, etc.); triazoles (e.g. 1-(p-chlorobenzenesulfonyloxy)-6-chloro-1H-benzotriazole, N-hydroxybenzotriazole, etc.); imidazoles (e.g. N,N'-carbonyldiimidazole, N,N'-carbonylbis(2-methylimidazole), etc.; ketenimine compounds (e.g. pentamethyleneketene-N-cyclohexylimine, diphenylketene-N-cyclohexylimine, etc.); ethoxyacetylene, 1-alkoxy-1-chloroethylenes; trialkyl phosphites; polyethyl phosphate; polyisopropyl phosphate; phosphorus oxychloride (phosphoryl chloride); diphenyl phosphorochloridate; triphenylphosphine; phosphorus trichloride; thionyl chloride; oxalyl chloride; halopyridinium salts (e.g. 2-chloro-1-methylpyridinium iodide etc.); cyanuric chloride; lower alkyl haloformates (e.g. ethyl chloroformate, isopropyl chloroformate, etc.); 2-ethyl-7-hydroxybenzisoxazolium salts; 2-ethyl-5-(m-sulfophenyl)isoxazolium hydroxide internal salt; Vilsmeier reagents prepared by reacting N,N-dimethylformamide with thionyl chloride, phosgene, trichloromethyl chloroformate, phosphorus oxychloride, etc., respectively.

This reaction can also be conducted in the presence of an inorganic or organic base, for example alkali metal hydroxides (e.g. sodium hydroxide, potassium hydroxide, etc.), alkali metal carbonates (e.g. sodium carbonate, potassium carbonate, etc.), alkali metal hydrogen-carbonates (e.g. sodium hydrogencarbonate, potassium hydrogencarbonate, etc.), tri (lower) alkylamines (e.g. trimethylamine, triethylamine, etc.), pyridine and its derivatives (e.g. N,N-dimethylaminopyridine, 4-pyrrolidinopyridine, 4-piperazinopyridine, 4-(4-methylpiperidino)pyridine, etc. and their hydrochlorides, hydrobromides, etc.), N-(lower) alkylmorpholines (e.g. N-methylmorpholine etc.), and N,N-di(lower)alkylbenzylamines, and so on.

Step 2

Compound (VII) or a salt thereof can be produced by reacting compound (V) or a reactive derivative of the carboxyl group thereof, or a salt thereof, with compound (VI) or a reactive derivative of the amino group thereof, or a salt thereof.

This reaction can be carried out substantially in the same manner as the reaction in Step 1. Therefore-, with regard to the procedure and conditions (e.g. solvent, reaction temperature, etc.) of this reaction, reference should be made to the description of Step 1.

Step 3

Compound (VIII) or a salt thereof can be produced by reacting compound (VII) or a reactive derivative of the amino group thereof, or a salt thereof, with compound (IV) or a reactive derivative of the carboxyl group thereof, or a salt thereof.

This reaction can be carried out substantially in the same manner as the reaction in Step 1. Therefore, with regard to the procedure and conditions (e.g. solvent, reaction temperature, etc.) of this reaction, reference should be made to the description of Step 1.

Step 4

Compound (I) or a salt thereof can be produced by subjecting compound (VIII) or a reactive derivative of its carboxyl group, or a salt thereof, to cyclization reaction.

The preferred reactive derivative of the carboxyl group of compound (VIII) includes the same species as those mentioned by way of example in the description of Step 1.

This reaction is carried out by the conventional method for cyclization, for example under heating or in the presence of a condensing agent. The preferred condensing agent includes the same substances as mentioned by way of example in the description of Step 1.

This reaction can also be conducted in the presence of an inorganic or organic base, for example alkali metal hydroxides (e.g. sodium hydroxide, potassium hydroxide, etc.), alkali metal carbonates (e.g. sodium carbonate, potassium carbonate, etc.), alkali metal hydrogencarbonates (e.g. sodium hydrogencarbonate, potassium hydrogencarbonate, etc.), tri(lower)alkylamines (e.g. trimethylamine, triethylamine, etc.), pyridine and its derivatives (e.g. N,N-dimethylaminopyridine, 4-pyrrolidinopyridine, 4-piperazinopyridine, 4-(4-methylpiperidino)pyridine, and their hydrochlorides, hydrobromides, etc.), N-(lower) alkylmorpholines (e.g. N-methylmorpholine etc.), and N,N-di(lower)alkylbenzylamines, and so on.

This reaction in the presence of a condensing agent is generally carried out in the common solvent such as chloroform, tetrahydrofuran, N,N-dimethylformamide, alcohol (e.g. methanol, ethanol, propanol, etc.), acetonitrile, pyridine, 4-methyl-2-pentanone, benzene, toluene, xylene, etc., a mixture of such solvents, or an arbitrary other organic solvent which does not interfere with the reaction.

There is no particular limitation on the reaction temperature but the reaction is usually carried out under cooling, at room temperature, or at elevated temperature.

The cyclization reaction under heating can be carried out in said organic solvent under heating at a temperature not exceeding the boiling point of the solvent.

When $R_1$, $R_2$ and $R_{11}$ of compounds (IV), (VII), (VIII) and their salts have been protected, the hydroxyl-protecting group, carboxyl-protecting group or amino-protecting group may be eliminated by a deprotection reaction.

The deprotection reaction is carried out by the routine procedure for removing a hydroxyl-protecting group, a carboxyl-protecting group or an amino-protecting group, for example by hydrolysis or reduction.

The hydrolysis is preferably carried out in the presence of a base or an acid (inclusive of a Lewis acid)

The preferred base includes inorganic and organic bases such as alkali metals (e.g. sodium, potassium, etc.), alkaline earth metals (e.g. magnesium, calcium, etc.), the hydroxides, carbonates or hydrogen-carbonates of said metals, alkali metal alkoxides (e.g. sodium methoxide, sodium ethoxide, potassium t-butoxide, etc.), alkali metal acetates, alkaline earth metal phosphates, alkali metal hydrogenphosphates (e.g. disodium hydrogenphosphate, dipotassium hydrogenphosphate, etc.), tri(lower)alkylamines (e.g. trimethylamine, triethylamine, etc.), pyridine and its derivatives (e.g. picoline, lutidine, 4-dimethyl-aminopyridine, etc.), N-(lower)alkylmorpholines (e.g. N-methylmorpholine etc.), 1,5-diazabicyclo[4.3.0]-non-5-ene, 1,4-diazabicyclo[2.2.2]octane, 1,8-diazabicyclo[5.4.0]undec-7-ene, and quinoline, among others.

The preferred acid includes organic acids (e.g. formic acid, acetic acid, propionic acid, trichloroacetic acid, trifluoroacetic acid, etc.) and inorganic acids (e.g. hydrochloric acid, hydrobromic acid, sulfuric acid, etc.) The deprotection reaction using a trihaloacetic acid (e.g. trichloroacetic acid, trifluoroacetic acid, etc.) can be accelerated by adding a cation scavenger (e.g. phenol, anisole, etc.).

This hydrolysis reaction is generally conducted in the common solvent such as water, alcohol (e.g. methanol, ethanol, etc.), diethyl ether, dioxane, tetrahydrofuran, dichloromethane, ethyl acetate, etc., a mixture of such solvents, or a suitable other organic solvent that does not interfere with the reaction. When the above-mentioned base or acid is a liquid, the base or acid may be used as the solvent as well.

There is no particular limitation on the reaction temperature but the reaction is generally conducted under cooling, at room temperature, or at elevated temperature.

The reduction method which can be applied to the deprotection reaction includes chemical reduction and catalytic reduction.

The preferred reducing agent which can be used in chemical reduction includes but is not limited to various combinations of a metal (e.g. tin, zinc, iron, etc.) or a metal compound (e.g. chromium chloride, chromium acetate, etc.) with an organic or inorganic acid (e.g. formic acid, acetic acid, propionic acid, trifluoroacetic acid, p-toluenesulfonic acid, hydrochloric acid, hydrobromic acid, etc.).

The preferred catalyst which can be used for the catalytic reduction includes but is not limited to the common catalysts such as platinum catalysts (e.g. platinum plate, platinum sponge, platinum black, colloidal platinum, platinum oxide, platinum wire, etc.), palladium catalysts (e.g. palladium sponge, palladium black, colloidal palladium, palladium oxide, palladium-carbon, palladium-barium sulfate, palladium-barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced ion, Raney ion, etc.), and copper catalysts (e.g. reduced copper, Raney copper, Ullmann copper, etc.).

The reduction reaction is generally carried out in a solvent which does not interfere with the reaction, such as water, alcohol (e.g. methanol, ethanol, propanol, etc.), N,N-dimethylformamide, etc., or a mixture of such solvent. When the above-mentioned acid for use in chemical reduction is a liquid, the acid can be used as the solvent as well. The preferred solvent for catalytic reduction includes not only the above-mentioned solvents but also such common solvents as diethyl ether, dioxane, tetrahydrofuran, etc. and mixtures thereof.

There is no particular limitation on the reaction temperature for this reduction but the reduction reaction is generally conducted under cooling, at room temperature, or at elevated temperature.

The compounds obtained in the respective production steps described above can be separated and purified by the conventional procedures such as, for example, extraction, precipitation, recrystallization, column chromatography, and recrystallization.

The starting compounds to be used in the above respective steps can be prepared by the processes described hereinafter in production examples.

While compound (I) through compound (VIII) may include one or more stereoisomers due to asymmetric carbon, such isomers and mixtures thereof also fall within the scope of the invention.

The depsipeptide derivative (I) and its pharmaceutically acceptable salt include solvates [for example inclusion compounds (e.g. hydrates, etc.)].

In accordance with this invention there is provided a commercially advantageous alternative process for producing the cyclodepsipeptide derivative (I), a compound having high vermicidal activity for use as an anthelmintic in animals and man.

The following production examples and examples illustrate this invention in further detail.

PRODUCTION EXAMPLE 1

Diisopropylethylamine (1.15 ml) and chloromethyl methyl ether (0.5 ml) were added to a solution of benzyl (R)-2-hydroxyl-3-(4-morpholinophenyl)propionate (1.5 g) in dichloromethane (15 ml) under ice-cooling and the mixture was stirred at room temperature for 19 hours. This reaction mixture was diluted with water (40 ml) and extracted with ethyl acetate (20 ml×3). The organic layer was washed serially with 5% sodium hydrogencarbonate solution (20 ml), water (20 ml) and saturated aqueous solution of sodium chloride (20 ml) in the order mentioned and dehydrated over anhydrous sodium sulfate and the solvent was then distilled off under reduced pressure. The resulting crude product was purified by silica gel column chromatography, elution being carried out with hexane-ethyl acetate (1:2, v/v). From the fraction containing the objective compound, the solvent was distilled off under reduced pressure to provide 1.73 g of benzyl (R)-2-methoxymethoxy-3-(4-morpholinophenyl)propionate.

$^1$H-NMR (CDCl$_3$; δ): 2.84–3.10 (2H, m), 3.07–3.19 (4H, m), 3.13 (3H, s), 3.80–3.94 (4H, m), 4.32 (1H, dd), 4.53 (1H, d), 4.64 (1H, d), 5.14 (2H, s), 6.81 (2H, d), 7.12 (2H, d), 7.23–7.41 (5H, m) APCI-MS (M+H)$^+$=386

PRODUCTION EXAMPLE 2

To a solution of benzyl (R)-2-methoxymethoxy-3-(4-morpholinophenyl)propionate (1.66 g) in methanol (8.6 ml) was added 10% palladium-carbon (0.2 g), and hydrogenation was carried out in a hydrogen atmosphere at atmospheric pressure and room temperature for 100 minutes. After the catalyst was filtered off, the solvent was distilled off under reduced pressure. The residue was further subjected to azeotropic distillation with isopropyl ether-hexane to provide 1.44 g of (R)-2-methoxymethoxy-3-(4-morpholino-phenyl)propionic acid.

$^1$H-NMR (CDCl$_3$; δ): 2.88–3.10 (2H, m), 3.08–3.10 (4H, m), 3.17 (3H, s), 3.78–3.92 (4H, m), 4.34 (1H, dd) 4.52 (1H, d), 4.66 (1H, d), 6.86 (2H, d), 7.18 (2H, d)

EXAMPLE 1

To a mixture of MOM-D-p-MorPhLac-OH (1.18 g), H-MeLeu-D-Lac-OBzl (0.87 g), N-methylmorpholine (1.06 ml) and acetonitrile (15 ml) was added diphenyl phosphorochloridate (1.29 g) under ice-cooling, and the mixture was stirred under the same conditions for 90 minutes. The solvent was then distilled off under reduced pressure and the residue was diluted with water (40 ml) and extracted with isopropyl ether (20 ml×3). The isopropyl ether layer was serially washed with 5% sodium hydrogencarbonate solution (20 ml), water (20 ml) and saturated aqueous solution of sodium chloride (20 ml) in the order mentioned and dehydrated over anhydrous sodium sulfate. After the sodium sulfate was filtered off, the filtrate was passed through silica gel (2 g) and the solvent was distilled off under reduced pressure to provide 2.08 g of MOM-D-p-MorPhLac-MeLeu-D-Lac-OBzl.

$^1$H-NMR (CDCl$_3$; δ): 0.86 (6H, d), 1.46 (3H, d), 1.41–1.80 (3H, m), 2.78–3.02 (5H, m), 3.05–3.22 (7H, m), 3.78–3.93 (4H, m), 4.42–4.77 (3H, m), 5.01–5.20 (3H, m), 5.38–5.51 (1H, m), 6.87 (2H, d), 7.18 (2H, d), 7.20–7.40 (5H, m) APCI-MS (M+H)$^+$=585

EXAMPLE 2

Using MOM-D-p-MorPhLac-MeLeu-D-Lac-OBzl (2.06 g) in lieu of benzyl (R)-2-methoxymethoxy-3-(4-morpholinophenyl)propionate, the procedure of Production Example 2 was otherwise repeated to provide 1.72 g of MOM-D-p-MorPhLac-MeLeu-D-Lac-OH.

$^1$H-NMR (CDCl$_3$; δ): 0.87 (3H, d); 0.88 (3H, d), 1.49 (3H, d), 1.50–1.93 (3H, m), 2.78–3.30 (12H, m), 3.80–3.96 (4H, m), 4.50–4.80 (3H, m), 5.10 (1H, dd), 5.31 (1H, dd), 6.87 (2H, d), 7.17 (2H, d)

EXAMPLE 3

Using Boc-MeLeu-D-p-MorPhLac-MeLeu-D-Lac-OH (2.48 g) in lieu of MOM-D-p-MorPhLac-OH and HCl.H-MeLeu-OBzl (0.95 g) in lieu of H-MeLeu-D-Lac-OBzl, the procedure of Example 1 was otherwise repeated to provide 4.05 g of Boc-MeLeu-D-p-MorPhLac-MeLeu-D-Lac-MeLeu-OBzl.

$^1$H-NMR (CDCl$_3$; δ): 0.78–1.03 (18H, m), 1.2–1.98 (21H, m), 2.73–3.20 (15H, m), 3.80–3.97 (4H, m), 4.63–4.80 (m) & 4.91–5.04 (m) & 5.10–5.34 (m) (7H), 6.86 (2H, d), 7.15 (2H, d), 7.20–7.40 (5H, m) FAB-MS (M−Boc+H)$^+$=795

EXAMPLE 4

In 4N hydrogen chloride in ethyl acetate (18 ml) was dissolved 4.04 g of Boc-MeLeu-D-p-MorPhLac-MeLeu-D-Lac-MeLeu-OBzl under ice-cooling, and the mixture was stirred under the same conditions for 1 hour. The solvent was then distilled off under reduced pressure and the residue was subjected twice to azeotropic distillation with ethyl acetate-toluene to provide 4.16 g of 2HCl.H-MeLeu-D-p-MorPhLac-MeLeu-D-Lac-MeLeu-OBzl.

$^1$H-NMR (CDCl$_3$; δ) 0.78–1.10 (18H, m), 1.22–2.00 (12H, m), 2.58–3.34 (11H, m), 3.38–3.58 (4H, m), 3.76–3.92 (1H, m), 4.13–4.41 (4H, m), 4.58–4.77 (m) & 4.97–5.63 (m) (6H), 7.10–7.42 (5H, m)), 7.47 (2H, d), 7.74 (2H, d), 9.35–9.60 (1H, m), 10.14–10.50 (1H, m)

EXAMPLE 5

To a mixture of MOM-D-p-MorPhLac-MeLeu-D-Lac-OH (1.71 g), 2HCl.H-MeLeu-D-p-MorPhLac-MeLeu-D-Lac-MeLeu-OBzl (4.15 g), N-methylmorpholine (1.54 ml) and acetonitrile (14 ml) was added diphenyl phosphorochloridate (0.9 g) under ice-cooling, and the whole mixture was stirred under the same conditions for 3 hours. Then, N-methylmorpholine (0.18 ml) and diphenyl phosphorochloridate (0.45 g) were further added and the mixture was stirred as it was for 30 minutes. The solvent was then distilled off under reduced pressure and the residue was diluted with water (40 ml) and extracted with ethyl acetate (20 ml×3). The ethyl acetate layer was serially washed with 5% sodium hydrogen carbonate solution (20 ml), water (20 ml) and saturated aqueous solution of sodium chloride (20 ml) in the order mentioned and dehydrated over anhydrous sodium sulfate and the solvent was distilled off under reduced pressure. The residual crude product was purified by silica gel column chromatography, elution being carried out with hexane-ethyl acetate-ethanol (55/40/5, v/v/v). From the fraction containing the objective product, the solvent was distilled off under reduced pressure to provide 3.39 g of MOM-D-p-MorPhLac-MeLeu-D-Lac-MeLeu-D-p-MorPhLac-MeLeu-D-Lac-MeLou-OBzl.

$^1$H-NMR (CDCl$_3$; δ) 0.70–1.03 (24H, m), 1.03–1.92 (18H, m), 2.72–3.21 (27H, m), 3.72–3.95 (8H, m), 4.36–4.81 (m) & 4.96–5.05 (m) & 5.05–5.56 (m) (12H), 6.82 (4H, d), 7.03–7.42 (9H, m). FAB-MS (M+H)$^+$=1271

EXAMPLE 6

Using MOM-D-p-MorPhLac-MeLeu-D-Lac-MeLeu-D-p-MorPhLac-MeLeu-D-Lac-MeLeu-OBzl (0.21 g) in lieu of benzyl (R)-2-methoxymethoxy-3-(4-morpholinophenyl)-propionate, the procedure of Production Example 2 was otherwise repeated to provide 0.18 g of MOM-D-p-MorPhLac-MeLeu-D-Lac-MeLeu-D-p-MorPhLac-MeLeu-D-Lac-MeLeu-OH.

$^1$H-NMR (CDCl$_3$; δ): 0.72–1.04 (24H, m), 1.04–1.91 (18H, m), 2.71–3.21 (27H, m), 3.79–3.97 (8H, m), 4.37–4.81 (m) & 4.90–5.60 (m) (10H), 6.82 (4H, d) 7.08–7.30 (4H, m) FAB-MS (M+Na)$^+$=1202

EXAMPLE 7

To a solution of MOM-D-p-MorPhLac-MeLeu-D-Lac-MeLeu-D-p-MorPhLac-MeLeu-D-Lac-MeLeu-OH (0.45 g) in dichloromethane (2.5 ml) was added trifluoroacetic acid (2.5 ml) under ice-cooling, and the mixture was stirred as it was for 18 hours. The solvent was then distilled off under reduced pressure. Then, ethyl acetate (20 ml) and water (20 ml) were added to the residue and its pH was adjusted to 7 with 5% sodium hydrogencarbonate. After the ethyl acetate layer was separated, the aqueous layer was extracted with ethyl acetate (20 ml×2) The organic layers were combined, washed with saturated aqueous solution of sodium chloride (20 ml) and dehydrated over anhydrous sodium sulfate. The solvent was then distilled off under reduced pressure to provide 0.46 g of H-D-p-MorPhLac-MeLeu-D-Lac-MeLeu-D-p-MorPhLac-MeLeu-D-Lac-MeLeu-OH.

$^1$H-NMR (CDCl$_3$; δ): 0.70–1.05 (24H, m), 1.16–1.90 (18H, m), 2.70–3.36 (24H, m), 3.78–3.92 (8H, m), 4.50–4.78 (m) & 4.83–5.01 (m) & 5.18–5.56 (m) (8H) 6.79–6.94 (4H, m), 7.03–7.21 (4H, m) FAB-MS (M+H+Na)$^+$=1159

EXAMPLE 8

To ethanol-free chloroform (43.7 ml) were added dicyclohexylcarbodiimide (162.8 mg), dimethylaminopyridine (145.4 mg) and dimethylaminopyridine hydrochloride (125.1 mg), followed by refluxing at 75° C. To this mixture was added a solution of H-D-p-MorPhLac-MeLeu-D-Lac-MeLeu-D-p-MorPhLac-MeLeu-D-Lac-MeLeu-OH (448 mg) in chloroform (9 ml) over 4.5 hours, and the mixture was further refluxed for 3.5 hours. Then, cyclohexylcarbodiimide (80 mg) was further added and the mixture was refluxed for 1 hour, followed by further addition of dicyclohexylcarbodiimide (80 mg), and the mixture was further refluxed for 1.5 hours. After the solvent was distilled off under reduced pressure, water (20 ml) and ethyl acetate (20 ml) were added to the residue and-the insoluble matter was filtered off. After the ethyl acetate layer was separated from the aqueous layer, the latter layer was further extracted with ethyl acetate (20 ml×2) and the ethyl acetate layers were combined. The combined ethyl acetate layer was serially washed with 5% sodium hydrogencarbonate solution (20 ml), water (20 ml) and saturated aqueous solution of sodium chloride (20 ml) in the order mentioned and dehydrated over anhydrous sodium sulfate. The solvent was then distilled off under reduced pressure and the residual crude product was purified by silica gel column chromatography, elution being carried out with hexane-ethyl acetate-ethanol (45/50/5, v/v/v). From the fraction containing the objective compound, the solvent was distilled off under reduced pressure to provide the following compound (116.2 mg).

```
┌─MeLeu──D-p-MorPhLac──MeLeu──D──Lac──MeLeu──D-p-MorPhLac──MeLeu──D──Lac─┐
│                                                                        │
└────────────────────────────────────────────────────────────────────────┘
```

The various physical constants of this objective compound were in agreement with the corresponding values mentioned in WO 93/19053.

$^1$H-NMR (CDCl$_3$; δ): 0.64–1.10 (24H, m), 1.20–2.00 (18H, m), 2.62–3.21 (24H, m), 3.76–3.95 (8H, m), 4.41–4.57 (m) & 5.01–5.72 (m) (8H), 6.82 (4H, d), 7.13 (4H, d)

What is claimed is:

1. A compound of the formula:

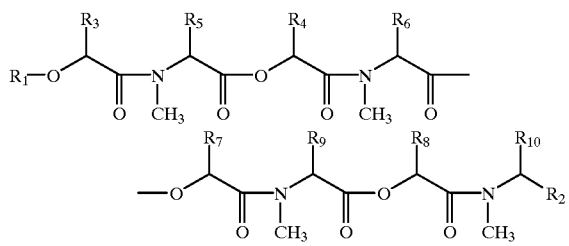

wherein $R_1$ represents hydrogen or a hydroxyl-protecting group; $R_2$ represents a carboxyl group or a protected carboxyl group; $R_3$, $R_4$, $R_7$ and $R_8$ each represents methyl or benzyl substituted by morpholino; $R_5$, $R_6$, $R_9$ and $R_{10}$ each represents isobutyl or a salt thereof.

2. The compound or its salt according to claim 1 wherein $R_3$ and $R_7$ each represents benzyl substituted by morpholino and $R_4$ and $R_8$ each represents methyl.

3. A process for producing a depsipeptide derivative or its salt characterized by subjecting a compound of the formula:

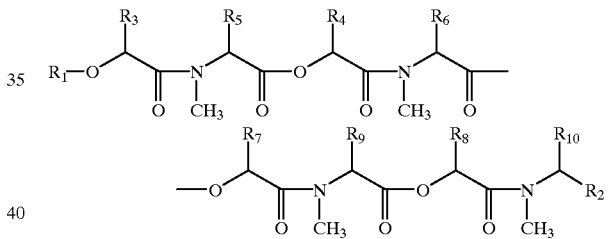

(wherein $R_1$ represents hydrogen or a hydroxyl-protecting group; $R_2$ represents a carboxyl group or a protected carboxyl group; $R_3$, $R_4$, $R_7$ and $R_8$ each represents a lower alkyl group, an aryl group or a substituted or unsubstituted aralkyl group; $R_5$, $R_6$, $R_9$ and $R_{10}$ each represents a lower alkyl group) or a reactive derivative of its carboxyl group, or a salt thereof, to cyclization reaction to give a compound of the general formula:

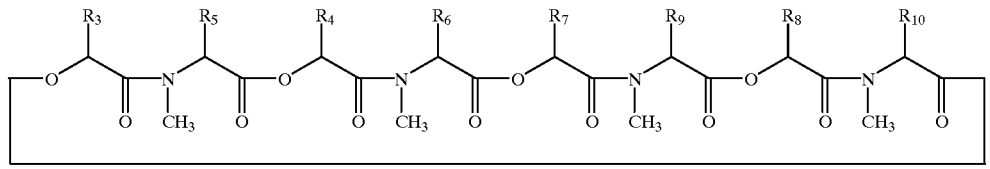

(wherein $R_3$, $R_4$, $R_7$ and $R_8$ each represents a lower alkyl group, an aryl group or a substituted or unsubstituted aralkyl group; $R_5$, $R_6$, $R_9$ and $R_{10}$ each represents a lower alkyl group) or a salt thereof.

4. The process of claim 3, wherein $R_3$, $R_4$, $R_7$ and $R_8$ each represents methyl or benzyl substituted by morpholino and $R_5$, $R_6$, $R_9$ and $R_{10}$ each represents isobutyl.

5. The process of claim 4, wherein $R_3$ and $R_7$ each represents benzyl substituted by morpholino and $R_4$ and $R_8$ each represents methyl.

* * * * *